(12) United States Patent
Hatton et al.

(10) Patent No.: US 6,635,024 B2
(45) Date of Patent: Oct. 21, 2003

(54) ARTICULATING KNEE SUPPORTS

(76) Inventors: Bobby Joe Hatton, Post Office Box 971, Mt. Ida, AR (US) 71957; Dale Lynn Hatton, Post Office Box 43, Sims, AR (US) 71969; Zane Grey Wallace, 98 Wallace Trail, Story, AR (US) 71970

( * ) Notice: Subject to any disclaimer, the term of this patent is extended or adjusted under 35 U.S.C. 154(b) by 68 days.

(21) Appl. No.: 09/854,440

(22) Filed: May 14, 2001

(65) Prior Publication Data

US 2002/0169402 A1 Nov. 14, 2002

(51) Int. Cl.[7] .................................................. A61F 5/00
(52) U.S. Cl. ........................................ 602/16; 602/26
(58) Field of Search ............................... 602/5, 16, 26; 623/39–44

(56) References Cited

U.S. PATENT DOCUMENTS

| | | | | | |
|---|---|---|---|---|---|
| 3,723,997 A | * | 4/1973 | Kolman | ............................ | 3/27 |
| 4,451,939 A | * | 6/1984 | Thompson | ........................ | 3/27 |
| 5,490,831 A | * | 2/1996 | Myers | ............................ | 602/26 |
| 6,159,248 A | * | 12/2000 | Gramnas | ....................... | 623/44 |

* cited by examiner

*Primary Examiner*—Michael A. Brown
(74) *Attorney, Agent, or Firm*—Dennis B. Haase

(57) ABSTRACT

An articulating knee brace in which opposed lockable knee joint assemblies conjoin femoral and tibial links and are selectively lockable to inhibit relative rotation of the knee joint of the wearer when the wearer stands or otherwise applies weight to a foot and releaseable to permit articulation of the knee joint when such weight is released.

18 Claims, 4 Drawing Sheets

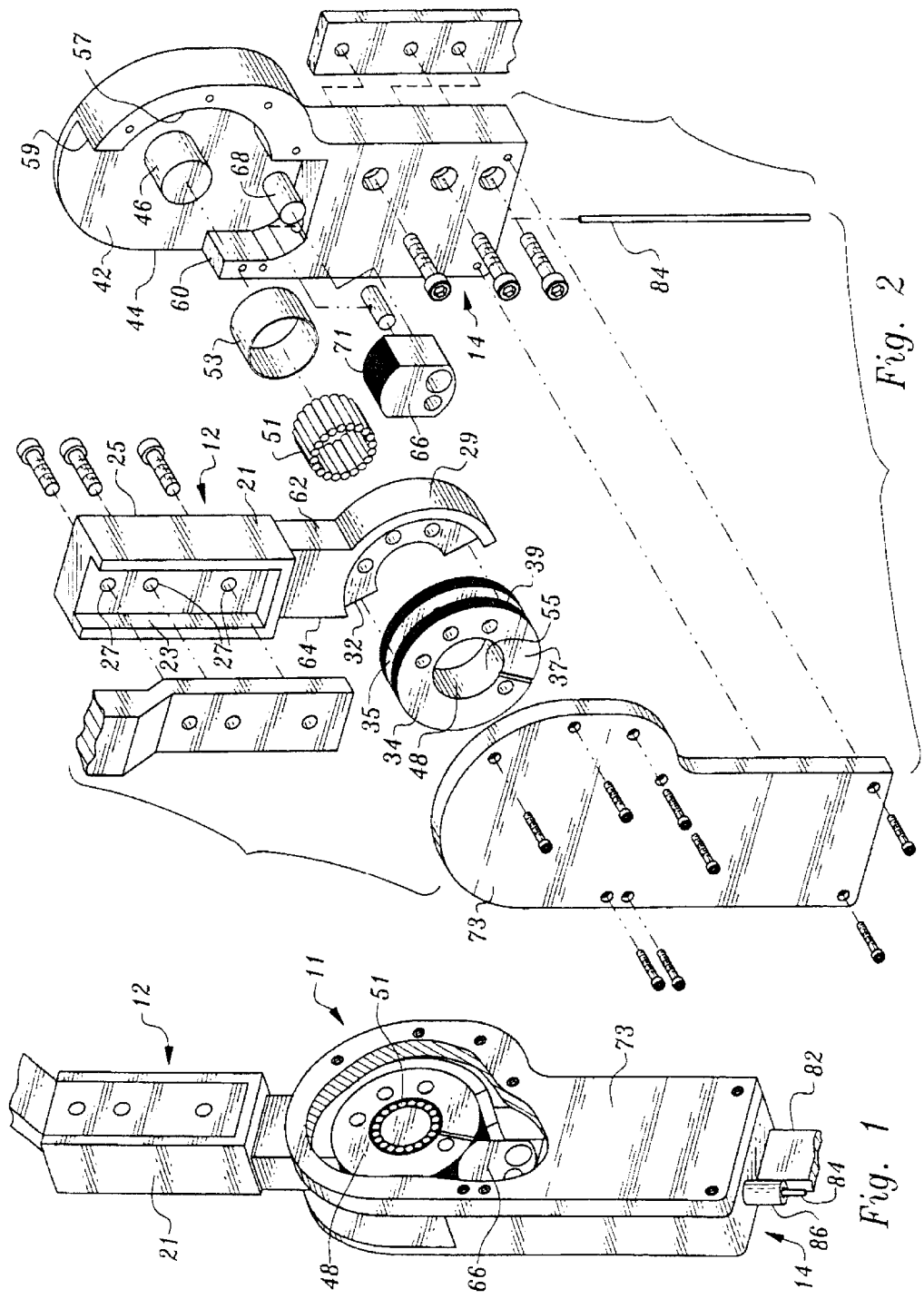

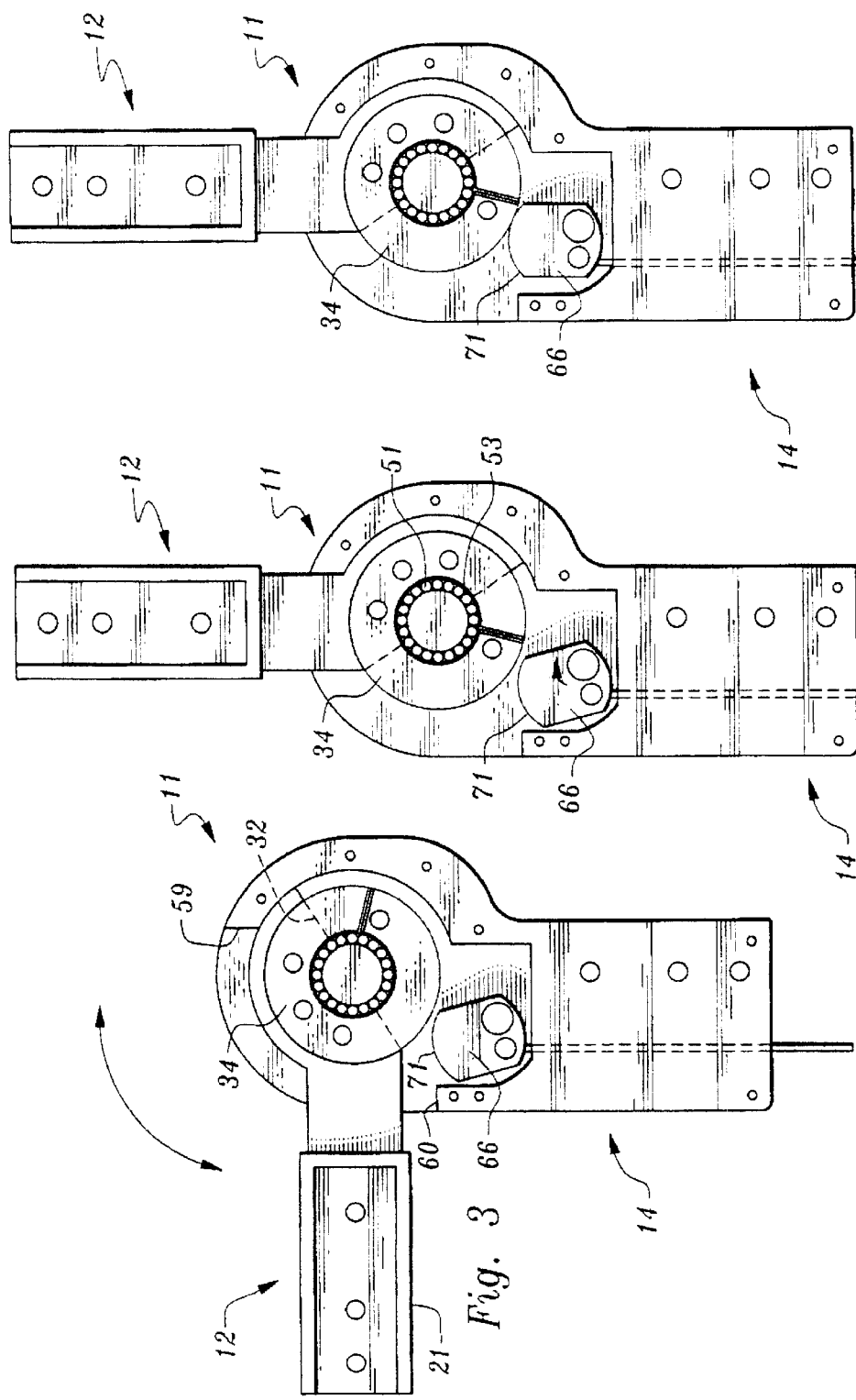

ARTICULATING KNEE SUPPORTS

The present invention relates generally to knee braces and, more particularly, to improvements in articulating joints therefor.

BACKGROUND OF THE INVENTION

1. Field of the Invention

Countless persons suffer, to a greater or lesser degree, from a loss of strength, or mobility, in one or both knees. The reasons for such conditions are numerous, and, in some instances, there is such a profound loss of strength in the joint that the person who finds it necessary to wear such a brace needs artificial support in order to rise from a sitting or similar position.

In such instances, it is common practice to permit locking of the articulating joint in order that the person wearing the brace can shift the load and call upon other muscles, not otherwise damaged, or at least lesser damaged, to stand, or otherwise move, even though the muscular structure which controls the knee is too weak to accomplish the act.

2. Overview of the Prior Art

The art in this discipline is indicative of the importance of such appliances and the effort that has gone into the search for a brace which adequately meets the needs of the widest possible spectrum of knee joint disabilities. Such efforts have grown beyond the private sector, and, as is evident from the Meyers et al. U.S. Pat. No. 5,490,831, the United States is actively engaged in the search for such a brace.

Meyers et al. discloses a selectively lockable joint for a knee brace in which a lever, which is mounted for limited rotation off center, is actuated by a stirrup attached to the foot to engage and disengage a clutch mechanism, which locks the joints of a knee brace in a predetermined position when substantial body weight is supported by the foot, and, of course, unlocks the joint when weight is relieved at the foot and limited flexibility, rather than rigidity, is not needed.

Barrack, Jr. U.S. Pat. No. 5,899,869 was issued over Meyers et al. '831 and discloses a ratchet type arrangement in the joint for essentially the same purposes as Meyers. To a similar effect, Clemens U.S. Pat. No. 6,001,875 teaches yet another gear arrangement in the joint and was also issued over the Meyers et al. '831 patent.

Finally, Barney U.S. Pat. No. 6,024,713 is illustrative of a very simple brace in which pivot joints move forwardly and to the rear, as the wearer moves, to tighten or release the cuff about the thigh to thereby provide stability as needed.

SUMMARY OF THE INVENTION

As is the case with the referenced prior art, the present invention constitutes a distinct improvement over Meyers et al. '831. The present invention eliminates much of the complicated mechanism of Meyers et al., such as the clutch mechanism and substitute therefor, and a wedge mechanism which is selectively engageable to lock and release the relatively movable elements of a joint for a knee brace.

Accordingly, it is an objective of the present invention to provide an articulating joint for a knee brace, which includes a greatly simplified mechanism for selectively locking and releasing the articulating elements of the joint. An objective related to the foregoing is to provide a joint mechanism as aforesaid which is highly efficient and functional.

Yet another objective of the present invention is to provide an articulating joint in which the relatively moveable elements thereof are selectively lockable by wedging those elements together and to accomplish the foregoing upon demand through the use of a foot controlled device which is responsive to body weight.

Another and still further objective of the present invention is to devise a joint mechanism which is simple, yet efficient, while providing the brace with which it functions with stability and mechanical reliability.

The foregoing, as well as other objects and advantages of the present invention, will become more evident with a study of the Detailed Description of a Preferred Embodiment presented hereinafter, when read in conjunction with the drawings, wherein:

DESCRIPTION OF THE DRAWINGS

FIG. 1 is a perspective view of the articulating joint of the present invention, with a portion of the cap cut away to illustrate the interrelation of parts of the joint as they would appear with the joint locked;

FIG. 2 is an exploded view of the joint of FIG. 1, providing a clear indication of the interrelationship of the parts of the joint;

FIG. 3 is a side elevation of the articulating joint of FIG. 1 with the cap removed to permit a clear view of the interaction of the wedge and showing the joint in an unlocked condition and the wearer of the brace in a sitting position;

FIG. 4 is a view similar to FIG. 3, except that the wearer is in an upright or standing position;

FIG. 5 is a view such as seen in FIG. 4, with the exception that the wearer of the brace to which the joint of the present invention is an integral part, is in the upright position with the joint locked;

DETAILED DESCRIPTION OF A PREFERRED EMBODIMENT

Figure 6:
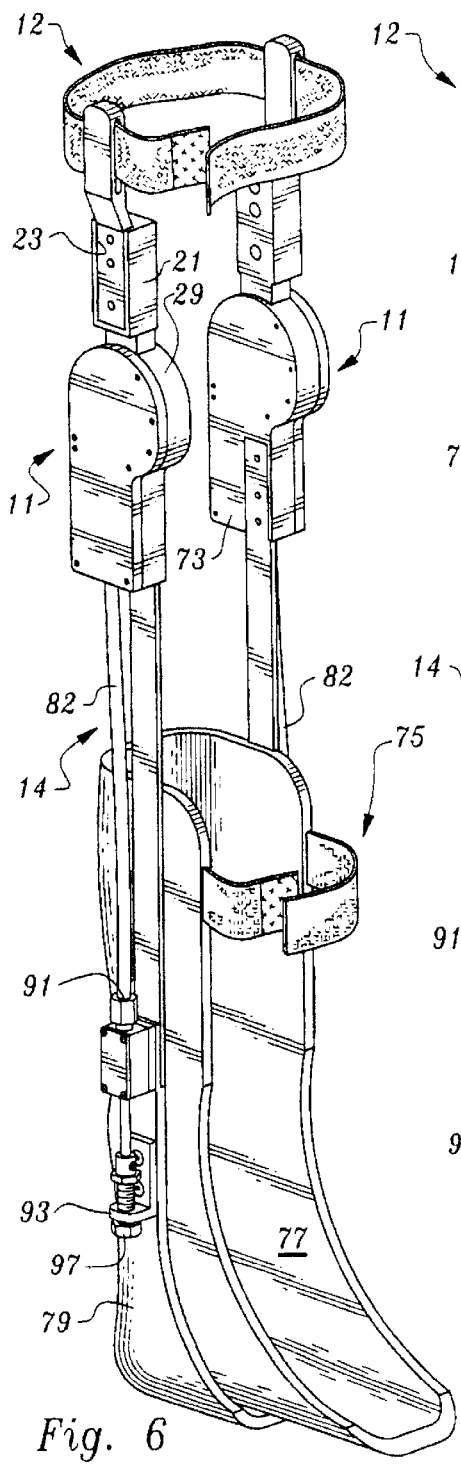
FIG. 6 is a pictorial representation, in perspective, of the total brace, illustrating the inner relationship of the various elements thereof.
Figure 7:
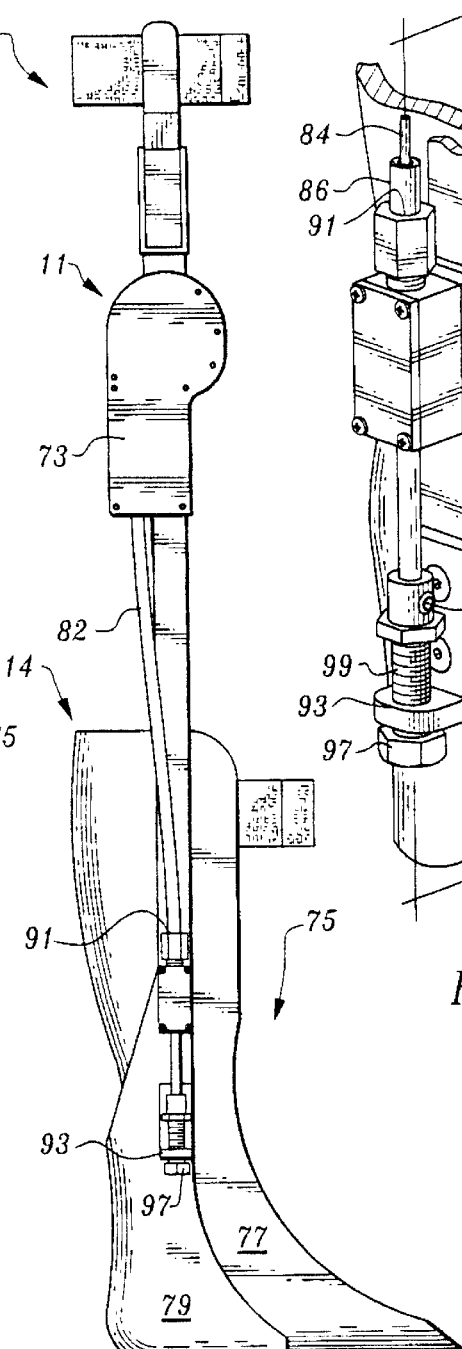
FIG. 7 is a side elevation of the brace of FIG. 6.
Figure 8:
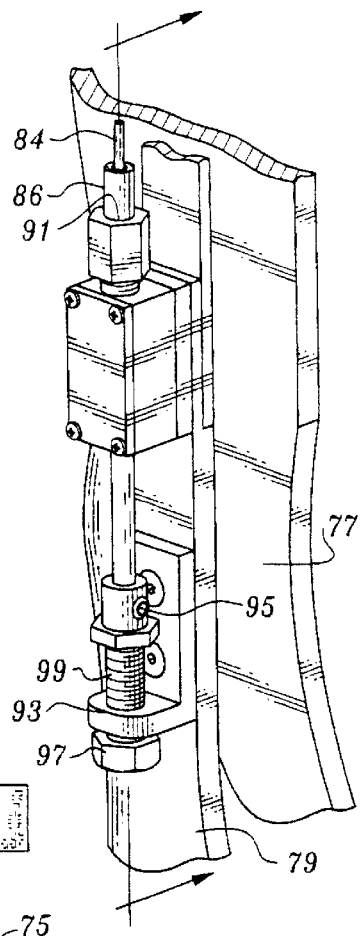
FIG. 8 is a partial section of the outer shell, illustrating the connection between the stirrup, shell and the lockable joint.
Figures 9, 10:
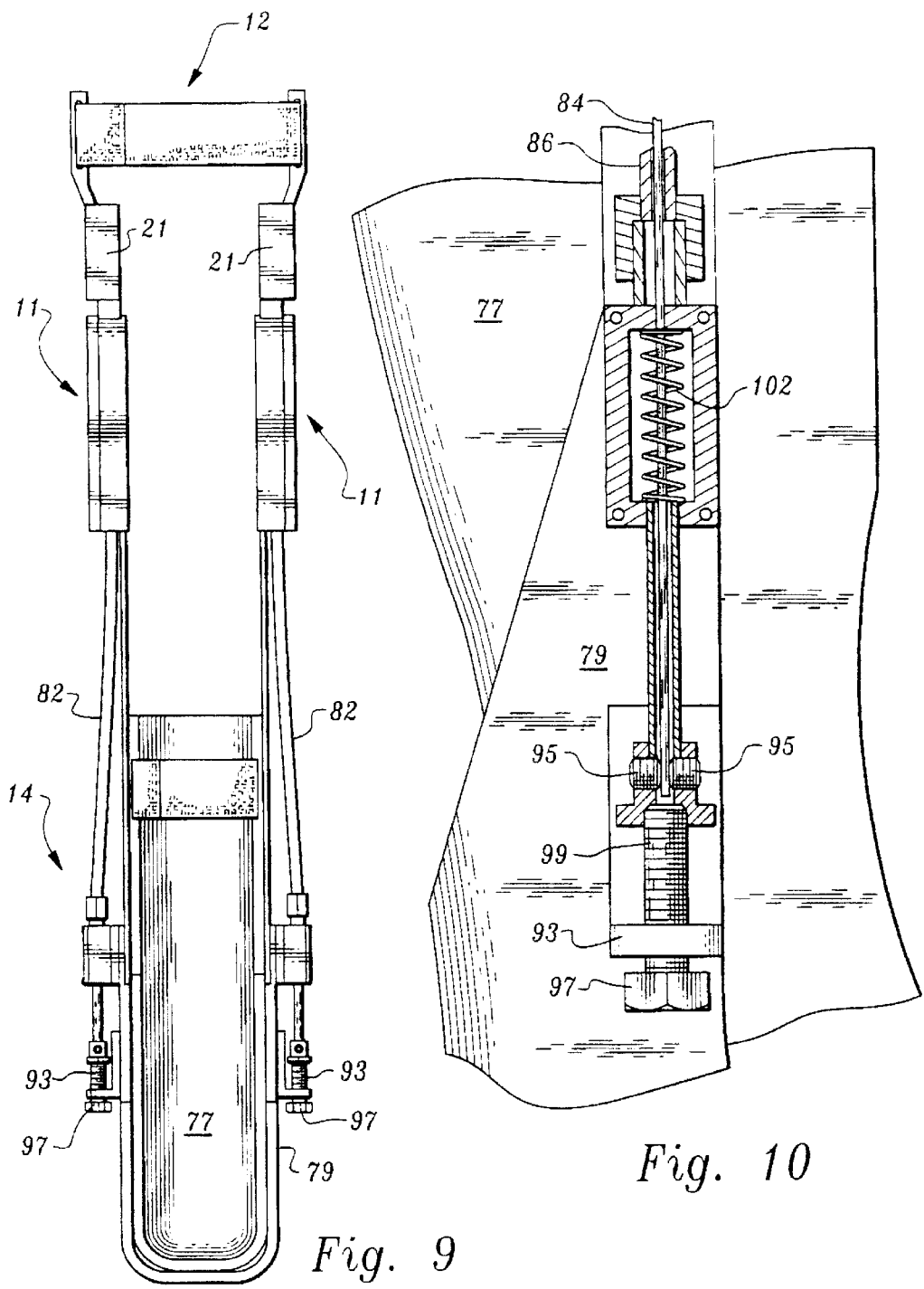
FIG. 9 is a front elevation of the brace of FIG. 6.
FIG. 10 is a partially sectioned view, similar to FIG. 8, with the internal mechanism exposed.

With reference now to the drawings, and initially to FIG. 1, an articulating joint 11, constructed in accordance with the present invention, is illustrated in considerable detail. The joint 11 has been devised to operate in concert with several knee brace configurations, not illustrated in any particular detail, worn by a person who has a weakened knee by virtue of traumatic injury or degenerative disease, which may or may not have required surgery, or some other debilitating remedial treatment. Typically, an articulating lockable knee joint assembly 11 is situated in the brace on both the medial and lateral sides of the knee joint at or about the horizontal plane of the patella where the femoral and tibial condyles meet.

The knee joint 11 joins together for relative rotation, a femoral link 12, which includes a femoral cuff, of any one of a number of well known configurations, which cuff encircles the thigh of the wearer in supporting relation thereto. The cuff is connected to, and supported by, at least one strut, not illustrated in any particular detail.

A tibial link 14 depends from, and is secured to, the femoral link for limited rotation thereabout. As in the case of the femoral cuff, there is typically a tibial cuff which encircles the calf and connects to the tibial link by means of struts, or the like.

In each joint 11, the femoral link 12 and tibial link 14 are essentially coplaner and relative rotation is within that plane.

Referring initially to the femoral link 12, an elongated member 21 is provided, which is formed, or otherwise provided, with a strut receiving pocket 23 at the upper end 25 of the member 21. Apertures 27 are provided to receive appropriate fasteners to thereby receive the strut within the pocket and secure it relative thereto.

The end of the member 21 remote from the upper end 23 is formed with an arcuate extension 29, having a central rib 32 which is contoured to have the same arc as formed on the extension 29. A friction ring 34 is formed with a slot 35 of size to receive the central rib, and appropriate fasteners are used to secure ring 34 on opposite sides of the central rib 32. It will be observed that the slot 35 is formed intermediate the side walls 37 of the ring 34.

In implementation of the principal purposes of the present invention, the circumferential surface 39 is roughened, such as by knurling, so as to provide a high friction surface.

Referring now to the tibial link 14, a recess 42 is formed in the upper portion 44 of the link 14. The recess is configured to receive the arcuate extension 29 of the femoral link 12. In order to position the arcuate extension properly within the recess 42, a post 46 is provided so as to receive the arcuate extension 29. A central bore 48 is provided in the ring 34 for that purpose.

It is an important feature of the joint 11 of the present invention that the links 12 and 14, when not locked, are rotatable relative to one another, in a smooth, essentially frictionless, manner. To this end, needle bearings 51 are provided, and an inner race 53 fits over the post and receives the needle bearings 51. In practice, the inner circumferential wall 55 of the bore 48 serves as the outer race for the needle bearings.

It will be seen that the recess 42 has an arcuate side wall 57 which has a diameter sufficient to receive the arcuate extension 29 of the femoral link without contact, but with minimal space in order that foreign materials can not readily accumulate.

In order to limit the rotation of the femoral link 12 relative to the tibial link 14, limit stops are provided at 59 and 60. As the link 12 moves, intermediate walls 62 and 64, respectively, will abut the stops 59 and 60, depending on the direction of movement, inhibiting further progress.

In order to selectively lock the femoral link 12 and tibial link 14, a wedge 66 is provided and mounted for limited rotation about a mounting pin 68. The wedge 66 is of a modified oval configuration and, in order to facilitate its movement, is mounted off center so that its rotation is eccentric relative to the ring 34. The surface 71 of the outer edge of the wedge 66 is knurled, or otherwise roughened, to provide a high friction surface. It will be appreciated, therefore, that the wedge is so positioned as to be movable on the eccentric toward and away from the knurled surface of the ring and, when in contact therewith, prevents movement of the femoral link relative to the tibial link, thereby locking the joint movement.

As a means of protecting the internal mechanism from dirt and the like, and also to prevent inadvertent contact with fingers and loose clothing, a cap 73 fits over and is fastened in any suitable fashion to the recess in the tibial link.

In order, in keeping with the present invention, to automatically lock and unlock the joint 11 in an essentially on demand manner, i.e., so that it is locked when weight is applied and support is most needed, a weight responsive mechanism is provided and is depicted in some considerable detail in FIG. 6.

To this end, a novel locking mechanism, in the nature of a wedge manipulator 75 is provided to accomplish this purpose. The wedge manipulator 75 is responsive to the position of the wearer in order that optimum support is achieved only as, and if, needed. Accordingly, a thin posterior heel stirrup, or cup, 77 is provided which circumscribes the heel of the wearer. The cup 77 is itself encased in an outer shell 79. The shell is, likewise, thin in order that both may fit into a shoe and is shaped to conform to the outer surface of the heel cup and is spaced by a small but finite amount from the heel cup such that relative movement toward one another is possible when the wearer moves, for example, from a position of repose to a standing position. A movement away from one another is accomplished when the weight of the body on the foot is relieved.

In order that the relative movement of the cup 77 and shell 79 may be transmitted to the joint 11, a bowden type cable 82 is provided. Such a cable is relatively well known and comprises an inner wire 84 encased in a sheath 86 and is movable relative thereto. The wire 84 is relatively flexible and may be made of any one of several suitable wear resistant materials, e.g., braided nylon, movable relative to a plastic sheath with minimal wear.

The wire 84, at its forward end 86, connects to the wedge 66. The post 68 upon which the wedge is mounted eccentrically for limited rotation, positions the wedge 66 relative to the ring 34 such that the roughened, or knurled, surface 71 of the wedge engages, in frictional relation, the circumferential surface 39 when weight of the wearer is applied to the cup 77 and the shell 79, and disengages when the weight is relieved.

The opposite, or remote end, 91 connects to the shell 79 by means of an adjustment bracket 93. The wire is clamped, or otherwise held, such as by set screws 95, in an adjustment screw 97. The adjustment screw 97 is positioned on a threaded post 99, rigidly positioned in the adjustment bracket 93. Thus, rotation of the adjustment screw will permit variation in the length of stroke of the wire relative to the sheath, and, thus, the force with which the wedge engages the circumferential surface of the ring. The sheath 86 is, in keeping with this aspect of the invention, fixed relative to the joint 11 and the heel cup 77 in any one of several well known means.

In assuring that the wire is as responsive to the release of pressure as it is to the application thereof, a spring mechanism 102 is provided which acts to retract the wire upon release of pressure on the cup and shell.

While it will be appreciated that some variation in the precise nature of the mechanism is anticipated without departure from the operation, a preferred embodiment of the present invention has been described in considerable detail and is now claimed as follows.

What is claimed is:

1. In an articulating knee brace, opposed lockable medial and lateral joint assemblies disposed between an upper femoral link adapted to embrace the thigh portion of the wearer's leg, and a lower tibial link section adapted to embrace the calf portion of the leg;

a locking joint mechanism, joining said femoral link and said tibial link, said mechanism including lockable medial and anterior joint assemblies, said assemblies being mirror images of one another; each said locking mechanism including a ring, a wedge situate in proximity to said ring, and said ring being connected to one of said upper and lower sections, said wedge being connected to the other of said one of said sections;

said wedge being movable into frictional contact with said ring when the weight of the wearer is applied to said brace, to thereby inhibit relative movement of said ring; and being moveable out of contact with said ring when said weight is relieved.

2. The articulating knee brace of claim 1, wherein stops are provided to limit rotation between said femoral link and said tibial link.

3. The articulating knee brace of claim 2, wherein adjustment is provided to establish the movement necessary to effect locking of said locking joint mechanism.

4. The articulating knee brace of claim 2, wherein said wedge having an oval shape, and being mounted to said tibial link.

5. The articulating knee brace of claim 2, wherein said wedge is mounted for limited rotation relative to said tibial link, said wedge being mounted for limited rotation near one end thereof off center, and having an edge, said edge being opposite said one end, and being roughened so as to create friction between said ring and said edge to thereby lock said locking joint mechanism.

6. The articulating knee brace of claim 1, wherein said wedge having an oval shape, and being mounted to said tibial link.

7. The articulating knee brace of claim 1, wherein said wedge is mounted for rotation into and out of contact with said ring.

8. The articulating knee brace of claim 1, wherein said wedge is mounted for limited rotation relative to said tibial link, said wedge being mounted for limited rotation near one end thereof off center, and having an edge, said edge being opposite said one end, and being roughened so as to create friction between said ring and said edge to thereby lock said locking joint mechanism.

9. The articulating knee brace of claim 1, wherein a bearing is provided between said femoral and said tibial links so as to enhance relative rotation between the two.

10. In an articulating knee brace, opposed lockable medial and lateral joint assemblies disposed between an upper femoral link adapted to embrace the thigh portion of the wearer's leg, and a lower tibial link section adapted to embrace the calf portion of the leg;

a locking joint mechanism, said locking joint mechanism connecting said femoral link and said tibial link for relative rotation, said mechanism including selectively lockable medial and anterior joint assemblies, said assemblies being mirror images of one another;

a wedge for locking and unlocking said locking joint mechanism, comprising a stirrup, said stirrup being formed to embrace the heel of the wearer beneath the calf portion of the wearers leg; a shell, said shell being formed to fit about said stirrup, said shell being mounted for limited movement toward and away from said stirrup;

a bowden type cable interconnecting said stirrup and said shell on the one hand, and said wedge mechanism on the other;

said shell being movable toward said stirrup when the wearer applies weight thereon, such moving causing locking of said locking joint mechanism, and said locking joint mechanism being unlocked when weight on said shell is relieved.

11. The articulating knee brace of claim 10, wherein stops are provided to limit rotation between said femoral link and said tibial link.

12. The articulating knee brace of claim 11, wherein said wedge having an oval shape, and being mounted to said tibial link.

13. The articulating knee brace of claim 11, wherein said wedge is mounted for limited rotation relative to said tibial link, said wedge being mounted for limited rotation near one end thereof off center, and having an edge, said edge being opposite said one end, and being roughened so as to create friction between said ring and said edge to thereby lock said locking joint mechanism.

14. The articulating knee brace of claim 10, wherein said wedge having an oval shape, and being mounted to said tibial link.

15. The articulating knee brace of claim 10, wherein said wedge is mounted for rotation into and out of contact with said ring.

16. The articulating knee brace of claim 10, wherein said wedge is mounted for limited rotation relative to said tibial link, said wedge being mounted for limited rotation near one end thereof off center, and having an edge, said edge being opposite said one end, and being roughened so as to create friction between said ring and said edge to thereby lock said locking joint mechanism.

17. The articulating knee brace of claim 10, wherein adjustment is provided to establish the movement necessary to effect locking of said locking joint mechanism.

18. The articulating knee brace of claim 10, wherein a bearing is provided between said femoral and said tibial links so as to enhance relative rotation between the two.

* * * * *